United States Patent [19]

Maas

[11] Patent Number: 4,533,628

[45] Date of Patent: Aug. 6, 1985

[54] COLONY HYBRIDIZATION METHOD

[75] Inventor: Renata Maas, Hastings, N.Y.

[73] Assignee: New York University, New York, N.Y.

[21] Appl. No.: 519,842

[22] Filed: Aug. 3, 1983

[51] Int. Cl.$^3$ .................. C12Q 1/68; C12P 19/34; C12N 1/20; C12N 1/06

[52] U.S. Cl. .................................. 435/6; 435/91; 435/253; 435/259; 435/805; 435/820; 436/63; 436/94

[58] Field of Search ............... 435/4, 6, 172.3, 317, 435/259, 91, 253, 805, 820; 422/56, 58; 436/63, 94

[56] References Cited

U.S. PATENT DOCUMENTS 4,358,535 11/1982 Falkow et al. ...................... 435/5

OTHER PUBLICATIONS

Grunstein et al., 1975, "Colony Hybridization: A Method for the Isolation of Cloned DNAs that Contain a Specific Gene", Proc. Natl. Acad. Sci. 272, pp. 3961–3965.

Salton et al., 1951, "Studies of the Bacterial Cell Wall", Biochimicaet Biophysica Acta, vol. 7, pp. 19–42.

Journal of Bacteriology, vol. 45, pp. 97–105, (1981), Mazaitis, Structure of a Naturally Occurring Plasmid with Genes for Enterotoxin Production and Drug Resistance.

Journal of General Microbiology, vol. 5, pp. 391–404, (1951), M. R. J. Salton, Adsorption of Cetytrimethylammonium Bromide by Bacteria, its Action in Releasing Cellular Constitutents and its Bactericidal Effects.

Nuclear Acids Research, vol. 7, pp. 2115–2136, (1979), Gergen, Filter Replicas and Permanent Collections of Recombinant DNA Plasmids.

Infection and Immunity, vol. 32, No. 2, pp. 661–667, (1981), Kaper et al., Molecular Characterization of Environmental and Nontoxigenic Strains of *Vibrio cholerae.*

Journal of Infectious Diseases, vol. 145, pp. 863–869, (1982), Moseley et al., Identification of Enterotoxigenic *Escherichia coli* by Colony Hybridization Using Three Enterotoxin Gene Probes.

Infection and Immunity, vol. 29, pp. 140–143, (1980), Reis et al., Transfer of a CFA/I-ST Plasmid Promoted by a Conjugative Plasmid in a Strain of *Escherichia coli* of Serotype O128ac:H12.

Proc. Nat. Acad. Sci., vol. 72, No. 10, pp. 3961–3965, (1975), Grunstein et al., Colony Hybridization: A Method for the Isolation of Cloned DNA's that Contain a Specific Gene.

Primary Examiner—Thomas G. Wiseman
Assistant Examiner—Joanne Giesser
Attorney, Agent, or Firm—Lyon & Lyon

[57] ABSTRACT

In the colony hybridization technique, bacterial colonies are replica-plated onto filter paper, and their DNA is hybridized with labeled DNA containing a specific sequence. A one-hundred fold increase in sensitivity is obtained by subjecting the colonies to a stream of steam in the presence of alkali for about three minutes prior to hybridization.

9 Claims, 1 Drawing Figure

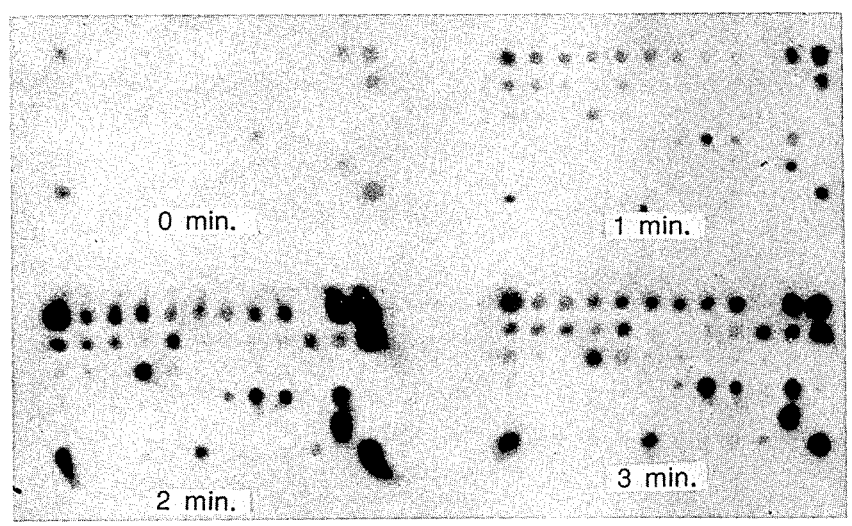

COLONY HYBRIDIZATION METHOD

LICENSE TO THE UNITED STATES GOVERNMENT

The government has an irrevocable, non-exclusive, non-transferrable, royalty free license in the invention described and claimed herein based upon research support from the National Science Foundation.

FIELD OF THE INVENTION

An improved colony hybridization method to screen bacterial colonies for a specified DNA sequence.

BACKGROUND OF THE INVENTION

Grunstein and Hogness, Proc. Natal. Acad. Sci. USA, 72, 3961–3965 (1975), described in 1975 a colony hybridization method which enabled them to screen for hybrid plasmids containing specified DNA sequences of genes. They lysed colonies in situ on nitrocellulose papers and fixed their denatured DNA, which was subsequently hybridized to specific labelled RNA and visualized by autoradiography. They were dealing with plasmid derivatives of ColEl, which would be present in large numbers (<10 per chromosome) and therefore their method was sufficiently sensitive for their purposes.

Gergen et al., Nucleic Acid Res., 7, 2115–2136 (1979), subsequently described a simpler and cheaper method, which involved lysing the cells on Whatman-brand 541 filter paper (a high wet strength paper). The DNA seemed to be immobilized very rapidly on this paper so that they were able to treat the filters in batch form without any special precautions. However, these investigators were also dealing with a multi-copy amplifiable plasmid, and they indeed amplified the plasmid by a chloramphenicol incubation step before lysing the colonies. An advantage of the 541 paper is that no baking of the papers is required to fix the DNA.

Kaper et al., Infec. Immun. 32, 661–667 (1981), adapted to colony hybridization method of Grunstein and Hogness to probe for the presence of cholera enterotoxin genes. Mosely et al., J. Infect. Dis., 145, 863–869 (1982), used this method to identify enterotoxigenic E. Coli strains by using three different enterotoxin gene probes. However, attempts by the present inventor to identify enterotoxigenic strains isolated from patients with diarrhea in Sao Paulo, Brazil have revealed that there are difficulties with heat-stable enterotoxin (ST) probes. The signal is often weak, and when compensated by exposing the films for longer time periods, the negative controls also gave a positive response.

SUMMARY OF THE INVENTION

The present invention provides an improved method of colony hybridization characterized by increased sensitivity and reliability. The improved method of the present invention increases the sensitivity of the colony hybridization method by about 100-fold. The increased sensitivity and reliability of the present invention will be useful in conducting routine diagnostic tests for which gene probes can be prepared.

The surprising and unexpected advantages of the present invention are achieved by introducing a steaming in the presence of alkali step, which is believed to lead to better lysis of the cells and denaturation of the DNA.

BRIEF DESCRIPTION OF THE DRAWING

Filter papers were prepared as described below, and steamed in the presence of alkali for varying lengths of time. The colonies represent different clinical isolates from Sao Paulo, Brazil, that are ST+ or ST−, and various K12 control strains including some unrelated cloned ST's. The controls are in positions D2, D3, D4, D5, and D6, all of which are negative. Letters are vertically down, and numbers are horizontal left to right.

DETAILED DESCRIPTION OF THE INVENTION

The present invention was tested by working with a plasmid described by Reis, Affonso, Trabulsi, Mazaitis, R. Maas and W. K. Maas, Infect. Immun., 29, 140–143 (1980). This plasmid codes for ST and CFA/I, and was tagged with kanamycin resistance and transferred into E. coli K12.

The strains to be probed were inoculated into wells of a 96-microtiter plate, where each well contained 150 μl of liquid rich medium. The bacteria were allowed to grow overnight at 37° C. (plate wrapped in tinfoil to prevent evaporation). Using a stainless steel multipronged device that fitted into the 96 wells, the different strains were transferred onto solid (2% agar) rich medium in a 150×25 mm plastic petri dish. (If the microtiter plate was kept subsequently as a stock, 75 μl of 80% glycerol was added to each well, the contents were mixed using the multipronged inoculator, and the wrapped plate was kept at −20° C.)

After overnight growth at 37° C., a sheet of suitable size Whatman-brand 541 filter paper was placed over the colonies. A glass spreader was used to remove any air bubbles that formed, as these prevent efficient transfer. The papers were left in place for 1–2 hours.

Each paper was then peeled off and treated as follows. It was placed colony side up on a suitable (132 mm diameter) sheet of 3 MM Whatman-brand paper in a Pyrex-brand petri dish in which the 3 MM paper had been saturated with 15 ml of a solution of 0.5M sodium hydroxide and 1.5M sodium chloride (lysing solution). Any trapped air bubbles were removed. The open Pyrex-brand dish was placed above boiling water in a covered kettle and the steaming was allowed to proceed for 3 minutes. The 541 paper was then immersed in fresh lysing solution at room temperature for 1 minute. If 6–8 papers were being treated serially, a 300 ml bath of lysing solution was used for the 1-minute wash. Each paper was then immersed in a solution of 1M Tris, pH 7 and 2M NaCl (neutralizing solution) for approximately 4 minutes. Again 300–500 ml of the latter was used to treat 6–8 papers serially. The papers were blotted on paper towels and air dried, usually at 37° C. They were then ready for hybridization, but could be kept indefinitely wrapped in tinfoil or in a petri dish.

The conditions for hybridization have been described (Gergen et al., supra.) The papers were equilibrated in hybridization solution at 37° C. for 2 hours. For the actual hybridization 20 ml of solution for each 96 cm² of paper was suitable and did not produce nonspecific binding, and 250 μg denatured calf thymus DNA per ml of hybridization volume was used as a carrier for the denatured labelled probe. The hybridization was carried out in plastic refrigerator dishes (10×14×6 cm) at 37° C. overnight with gentle agitation.

The ST probe used in the experiment described here consisted of a 510 base pair fragment containing part of an ST gene that had been isolated from a human *E. coli* strain and cloned with EcoR1 linkers into vector pACYC 184. The 510 base pair fragment was prepared by EcoR1 digestion of the plasmid DNA and purified by agarose gel electrophoresis. The fragment was labelled with $P^{32}$ by nick translation to a specific activity of approximately $5 \times 10^7$ cpm per $\mu$g ($1.37 \times 10^{-5}$ cpm per molecule of single stranded probe). The hybridization worked well in what was calculated to be a 3-fold excess of total probe to the total complementary DNA fixed to the paper(s).

After hybridization overnight, the papers were washed batch-wise 4 times in $2 \times SSC$ at room temperature, each time for 30 minutes. For 6 papers a 500 ml volume was used each time. They were blotted and air dried, usually at 37° C.

The papers were then exposed at room temperature to Kodak X-Omat Ar film sandwiched between two Dupont Cronex Par-Speed intensifying screens. One or two hours' exposure was sufficient for very clear results. A colony of a typical $ST^+$ clinical isolate bound the equivalent of 2,000 cpm (estimated by visual comparison to 2,000 cpm of $P^{32}$ spotted on paper and exposed to the same x-ray film). Under the described conditions, 2,000 cpm is equivalent to $1.5 \times 10^8$ molecules of single stranded probe.

The effect of different lengths of steaming time is shown in the FIGURE. After 2 minutes the plasmid DNA was probably totally denatured but not totally fixed, so that when the paper was removed from the petri dish some "smudging" occurred. Longer steaming (4 minutes) did not significantly increase the signal.

After steaming in alkali and the subsequent neutralization, the papers were allowed to hybridize in 50% formamide, $5 \times SSC$, $1 \times$ Denhardt's, 1 mM EDTA, 0.1% SDS, 250 $\mu$g/ml denatured calf thymus DNA and $P^{32}$ labelled denatured probe ($5 \times 10^7$ cpm per $\mu$g, 30 ng probe per paper) for 18 hours. The papers were washed 4 times in $2 \times SSC$ and exposed to Kodak X-Omat AR film for 2 hours with two intensifying screens. The colonies represent different clinical isolates from Sao Paulo that are $ST^+$ or $ST^-$, and various K12 control strains including some unrelated cloned ST's. The controls are in positions D2, D3, D4, D5 and D6, all of which were negative with the present probe. Letters vertically down; numbers horizontally left to right.

The results of steaming in the presence of alkali confirm that the total DNA fixed on the paper is limiting. This was also observed by Gergen et al., who found that amplification of their plasmid DNA resulted in a stronger signal. Reducing the probe by a factor of 5 from the 3-fold excess resulted in a weaker signal that was not enhanced by doubling the length of time of hybridization. This could prove quite useful in cases where the probe is contaminated with nonspecific sequences, because conceivably one could dilute out the probe contamination.

It is understood that various other modifications will be apparent to and can readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside the present invention, including all features which would be treated as equivalents thereof by those skilled in the art to which this invention pertains.

What is claimed is:

1. A colony hybridization method for detecting a specific DNA sequence comprising the following steps for performing the specified acts:
   growing bacterial colonies on agar and replicating them onto filter paper,
   steaming said colonies in the presence of alkali on said paper in order to lyse said colonies on said paper and release their DNA,
   fixing said DNA to said paper in situ,
   hybridizing DNA containing said specific sequence to a labelled DNA containing said specific sequence, and
   detecting said hybridized DNA containing said specific sequence.

2. The colony hybridization method according to claim 1, wherein said colonies are contacted with a stream of steam in the presence of alkali on said filter paper for at least one minute.

3. The colony hybridization method according to claim 1, wherein said colonies are contacted with a stream of steam in the presence of alkali for at least two minutes on said filter paper.

4. The colony hybridization method according to claim 1, wherein said colonies are contacted with a stream of steam in the presence of alkali for about three minutes.

5. The colony hybridization method according to claim 1, wherein said hybridized DNA is detected by autoradiography.

6. The colony hybridization method according to claim 5, wherein said hybridized DNA is detected by $P^{32}$-autoradiography.

7. The colony hybridization method according to claim 1, wherein said hybridized DNA is detected by fluorography.

8. The colony hybridization method according to claim 7, wherein said hybridized DNA is detected by $H^3$-fluorography.

9. The colony hybridization method according to claim 1, including preparing a reference set of said colonies by replica plating, and using said reference set as a control.

* * * * *